United States Patent [19]

Matson

[11] Patent Number: 5,104,639
[45] Date of Patent: Apr. 14, 1992

[54] METHOD FOR BIOLOGICAL TESTING AND/OR DEVELOPING PHARMACEUTICALS FOR TREATMENT OF DISORDERS USING ELECTROCHROMATOGRAPHY

[75] Inventor: Wayne R. Matson, Ayer, Mass.

[73] Assignee: ESA, Inc., Bedford, Mass.

[21] Appl. No.: 274,505

[22] Filed: Nov. 21, 1988

Related U.S. Application Data

[60] Division of Ser. No. 797,615, Nov. 13, 1985, Pat. No. 4,863,873, which is a continuation-in-part of Ser. No. 670,483, Nov. 13, 1984, abandoned, which is a continuation of Ser. No. 579,401, Feb. 17, 1984, Pat. No. 4,511,659, which is a continuation-in-part of Ser. No. 472,387, Mar. 4, 1983, abandoned, and a continuation-in-part of Ser. No. 425,183, Sep. 28, 1982, abandoned, which is a continuation of Ser. No. 111,917, Jan. 4, 1980, Pat. No. 4,404,065.

[51] Int. Cl.$^5$ .................. G01N 1/00; G01N 33/48; G01N 25/08; A61K 31/00
[52] U.S. Cl. .................. 424/2; 424/520; 424/530; 424/531; 424/545; 424/570; 73/61.1 C; 436/63; 436/150; 436/161; 204/153.1; 514/1
[58] Field of Search .................. 424/1.1, 2, 531, 520, 424/530, 545, 570; 436/63, 150, 161; 73/61.1 C; 204/153.1, 411, 412; 514/1, 2

[56] References Cited

U.S. PATENT DOCUMENTS

| | | | |
|---|---|---|---|
| 4,046,634 | 9/1977 | Mercer | 435/16 |
| 4,215,109 | 7/1980 | Rohenstroth-Bauer | 514/21 |
| 4,233,031 | 11/1980 | Matson et al. | 23/230 |
| 4,338,811 | 7/1982 | Miyagi et al. | 73/23.1 |
| 4,404,065 | 9/1983 | Matson | 204/1 T |
| 4,511,659 | 4/1985 | Matson | 436/150 |
| 4,863,873 | 9/1989 | Matson | 436/63 |

OTHER PUBLICATIONS

Guy, Michael N. et al., Analysis of Angiotensins I, II III and Iodinated Derivatives by High Performance Liquid Chromatrography, *Analytical Biochem.*, 112: 272-7 (1981).
Okwusaba, F. et al., Changes in Vasoactive Properties of Blood Products with Time and Attempted Identification of the Spasmogens, *Stroke* 12(6): 775-80 (1981).
Clin. Chem 30/9, pp. 1477-1488 (1984) Matson et al., "n-Electrode Three-Dimensional Liquid Chromatography with Electrochemical Detection for Determination of Neurotransmitters".
Journal of Liquid Chromatography, 6(2), pp. 375-381 (1983) Yamaguchi "Liquid Chromatographic Determination of Excretion Patterns of Urinary Phenolic Compounds".
Biological Markers in Psychiatry and Neurology, Proc. of a conference at Ochsner Clinic, New Orleans (1982), Schildkraut, "Biochemical Discrimination of Subgroups of Depressive Disorders Based on Differences in Catecholamine Metabolism" see pp. 23-33.
La Nouvelle Presse Medicalle, 9, pp. 2061-2063 (1980) Devynck et al., "Dosage rapide des Catecholamines Plasmatiques Pour le Diagnostic d'urgence des Pheochromocytomes".
Journal of Clinical Endocrinology and Metabolism, 50(5), pp. 857-861 (1980), Gullner et al., "Correction of Increased Sympathoadrenal Activity in Bartter's Syndrome by Inhibition of Prostaglandin Synthesis".

(List continued on next page.)

Primary Examiner—Richard L. Raymond
Assistant Examiner—Gary Hollinden
Attorney, Agent, or Firm—Hayes, Soloway, Hennessey & Hage

[57] ABSTRACT

A method for establishing a treatment protocol for correcting an abnormal condition or disease in a living organism is described. The method comprises the steps of analyzing body fluids from normal and abnormal individuals to generate analysis patterns of the normal and abnormal fluids, comparing the patterns to determine differences in the patterns, and establishing a treatment protocol for the abnormal individual through chemical or metabolic therapy which treating will normalize the abnormal pattern.

23 Claims, 9 Drawing Sheets

OTHER PUBLICATIONS

Archives of General psychiatry, 35, pp. 1427–1433 (1978) Schildkraut et al., "Toward a Biochemical Classification of Depressive Disorders".

British Medical Journal (1969) 2, 153–155, Marks et al., "Application of Urine Analysis to Diagnosis and Treatment of Heroin Addiction".

Clinical Pharmacology and Therapeutics, 7(6), pp. 727–739 (1966) Anton et al., "The Effect of Resperine on Catecholamine Metabolism and Behavior in Retarded Children".

Psychopharmacology (n.Y.) pp. 275–328 (1976) Schildkraut et al., "Biochemistry of Effective Disorders" CA85(25)190161d Abstract only.

Psychopharmacology (Berlin), 56(3), pp. 327–333, (1978) Schildkraut et al., "Opiates, Catecholanines, Behavior, and Mood" 89:53498n Abstract only.

Journal of American Geriatr. Soc., 25(7), pp. 289–298 (1977) Meyer et al., "Neurotransmitter Precursor Amino Acids in the Treatment of Multi-Infarct Dementia and Alzheimer's Disease" Index Medicus Journal Announcement: 7709 Abstract only.

A-MOBILE PHASE I
B-MOBILE PHASE II
C-MOBILE PHASE III

METHOD FOR BIOLOGICAL TESTING AND/OR DEVELOPING PHARMACEUTICALS FOR TREATMENT OF DISORDERS USING ELECTROCHROMATOGRAPHY

This is a divisional of co-pending application Ser. No. 797,615 filed on Nov. 13, 1985, U.S. Pat. No. 4,863,873, issued on Sept. 5, 1989, which is a continuation-in-part of 670,483 filed Nov. 13, 1984 abandoned, which in turn is in part a continuation of my copending application Ser. No. 06/579,401, filed Feb. 17, 1984, (now U.S. Pat. No. 4,511,659 issued Apr. 16, 1985), which is in part a continuation-in-part of my application Ser. No. 472,387 filed Mar. 4, 1983 (now abandoned), and in part a continuation of my copending application Ser. No. 425,183 now abandoned filed Sept. 28, 1982 which is, in turn, a continuation of my application Ser. No. 111,917 filed Jan. 4, 1984 (now U.S. Pat. No. 4,404,065 issued Sept. 13, 1983).

This invention relates to analytical systems, i.e. apparatus and methods for qualitatively and quantitatively testing materials in solution. The invention has particular utility for the detection and determination of biologically active materials such as neurotransmitters and other neurochemical substances in brain tissue, cerebrospinal fluid, plasma, serum, saliva, urine and the like, such as catecholamines, their precursors, cofactors and their metabolites. The invention is uniquely capable of generating analytical values and patterns of a large number of compounds of biological, diagnostic and pharmaceutical significance and of describing complex metabolic pathways of such substances from single small samples of biological materials and the use of such values and patterns for rational development of pharmaceuticals and will be described in connection with such utility although other uses are contemplated.

There is an extensive body of literature relating abnormalities in neurotransmitters, precursors, and metabolites to degenerative, neuropsychiatric and behavioral disorders, hypertension and certain carcinomas. See, for example, Schildkraut et al in *The Brain, Biochemistry and Behavior*, Proceedings of the Sixth, Arnold O. Beckman Conference in Clinical Chemistry, pages 47–68. Although the potential role of these compounds in a number of significant disorders has been established, their routine analysis has not yet achieved widespread clinical use. Two problems in the clinical utility of neurotransmitter measurements are related to the economic and technical limitations of current technology. First, there is felt to be a high degree of interlaboratory and intersample uncertainty in quantitative values. Second, it has been difficult to measure enough of the known metabolically related compounds of a particular neurotransmitter to fully describe its biochemical significance in an individual sample, or to detect, identify and measure unusual neurotransmitters—an important aspect of basic research in various disease states that is presently very expensive and specialized.

While a number of interlaboratory technique intercomparisons for a variety of neurotransmitters have been carried out, there has been no comprehensive study within and among different techniques and laboratories for neurotransmitters in typical samples of interest. In the absence of such studies, given the complexity of the analytical problem and the historically wide variation whenever an analyte has been subjected to rigorous interlaboratory testing, the current values for normal and abnormal neurotransmitter levels must be taken with unspecified and probably wide limits of confidence.

Although the analysis of single neurotransmitters or metabolites from a complex biochemical pathway has been shown to correlate with a number of disorders utilizing statistical analysis over a large number of samples, the analytical level of a single neurotransmitter in an individual sample, with a few exceptions, has had relatively low clinical diagnostic utility. Essentially the state of the field of biochemical correlates of disorders is that while between large populations of normal and abnormal individuals a correlation generally can be determined for a particular biochemical, the scatter that results from both analytical and biochemical phenomena typically does not permit the level of a particular biochemical to be utilized diagonostically for a particular single individual. Nor may a single biochemical value be utilized for the rational prescription or development of a pharmaceutical for that individual. This is not particularly surprising in that both the levels and effects of a particular neurotransmitter are modified by a number of other neurotransmitters in the same, or parallel metabolic pathways. If, for instance, 5-HT (serotonin) is to be used as a diagnostic tool for depression, suicidal tendencies, or schizophrenia, it would be necessary and perhaps provide a route to definitive diagnosis and pharmaceutical specification or development, to simultaneously determine the approximately 40 other compounds that derive from tryptophan and significantly effect the indolaminergic neuronal system's activity.

In recent years, LCEC (Liquid Chromatography with Electrochemical Detection) has become a common tool for the determination of catecholamines biogenic amines and their metabolites in biological fluids. Because of sensitivity limitations (typically 20–50 pg) and the complexity of biological samples, both separation and concentration steps typically have been necessary. Heretofore, plasma catecholamine analysis typically required three steps. First, the sample is collected and the catecholamines separated and concentrated, for example, using the alumina extraction procedure of Anton and Sayre (See A. H. Anton and D. F. Sayre, J. Pharmacol, Exp. Ther., 138 (1962), p. 360–375). The analytes, norepinephrine, epinephrine and dopamine, along with the internal standard DHBH (dihydroxybenzylamine), then are separated chromatographically, and finally detected electrochemically. Typical sample size requirements are 1.0 ml plasma or serum. In routine clinical use, there have been numerous problems with conventional techniques (alumina adsorption, ion exchange and extraction) due to a large number of poorly understood variables in the overall analysis system of sample acquisition, storage, preparation and sensor response. These problems have quite likely confused the relationships that may exist between levels and distribution of the catecholamines and various physiological and behavioral phenomena and disease states.

In the analysis of complex biological materials such as blood, serum and cerebrospinal fluids which may contain numerous different constituents, the important (e.g. abnormal) metabolites such as neurotransmitters to be identified may be present in only parts per trillion. While a chromatographic column can achieve macro separation of the various constituents it may not provide adequate spatial (in time) separation of the extremely small portion of metabolites of interest from the much larger percentage of the many other compounds coeluted from the column at the same time as the metabolites of interest. Many of these interfering coeluted materials are electrochemically active but electrochemically irreversible while many metabolites such as neurotransmitters are both electrochemically active and electrochemically reversible. It has been found that the analytical problems of reliable measurements of neurochemicals and related compounds are complicated by the fact that interferences with conventional or prior technologies are disorder related. This was discussed in my prior publication, (Matson et al, Clinical Chemistry, Vol. 30, No. 9, 1984) for dopamine, dopac and seratonin measurements in directly analyzed brain extract and cerebrospinal fluid for normal, schizphrenics and Alzheimers. Recent work has indicated that even for the widely used and accepted technique of alumina extraction for plasma catecholamines that inferences may be disorder specific. Higher values for Norepinephrine (NE) and Epinephrine (EP) were observed following alumina extraction and analysis of a single energy conventional electrochemical detector than for a three cell redox detector on neonatal stress blood samples. Analysis of the neonate extracts on the sixteen channel chemical imaging system revealed several unexpected compunds that are potential interferences including dihydroxyphenylacetic acid (DOPAC), 3-hydroxykynurenamine (3-OHKYA), and 3-hydroxyanthranilic acid (3-OHAN). These compounds have not been detected in normal adult plasma alumina extracts.

In my aforesaid U.S. Pat. No. 4,511,659, there is provided an electrochemical detection system comprising a plurality of coulometrically efficient electrochemical cells, in series, for sequentially oxidizing and reducing selected substances in a sample solution under controlled conditions prior to measurement on a downstream testing electrode or electrodes.

More specifically, in accordance with the invention provided in my aforesaid U.S. Pat. No. 4,511,659, a sample solution (e.g. a body fluid) is passed through a suitable chromatographic column and the eluant is streamed in contact with a series of electrochemically isolated, in-line coulometric electrodes operated under conditions so as to establish a series of "gates" for the sequential oxidation and reduction of substances in the sample solution whereby to screen (remove) selected interfering and electrochemically irreversible substances contained in the sample solution, while passing selected electrochemically reversible products for detection and measurement on a downstream electrode. The gate electrode series is followed in-line by one or more, preferably an array of six or more coulometric measuring electrodes, each formed of porous electrode base material such as fritted graphite, fritted carbon or other conductive fritted material, for detecting and measuring the electrochemically reversible compounds of interest (e.g. neurotransmitters).

As reported in my aforesaid U.S. Pat. No. 4,511,659, there are several beneficial effects of this approach to electrochemical analysis. Long-term drift in response is effectively eliminated by acquiring essentially 100% of the signal. The capability of analyzing essentially 100% of a material allows the assay of compounds of unknown purity by relating them to the basic principles of electrochemical reaction embodied in Faraday's Law. Poisoning of the electrode, a dominant problem with electrochemical sensors, is effectively eliminated by the use of a much larger relative surface area for reaction. And, finally, and most important tot he eventual development of array and gate cells, a coulometric electrode by virtue of its essentially 100% efficiency allows sequential oxidation and/or reduction of compounds at successive-in-line detectors. The improved sensitivity of the detection system as discussed in my aforesaid U.S. Pat. No. 4,511,659, particularly where two or more active testing electrodes follow the screening electrodes has given the ability to do direct injections of serum filtrates and has also allowed the generation of reproducible patterns of compounds with catecholamine like electrochemical behavior of a large number of resolvable components. This provides the possibility of performing pattern recognition for the diagnosis or perhaps even predictive diagnosis, of various disorders or disease states.

The present invention in broad aspect provides a system for resolving and detecting hundreds of compounds in a single sample at femtogram levels whereby to provide a small molecule inventory or metabolic pathway pattern of a individual. The small molecule inventory may be considered to reflect the underlying activity and distribution of the enzymatic pathways of an individual and hence reflect an operational measure of the genone determining those enzymes. The small molecule inventory of an individual may thus be used to determine the health state of the individual and/or to diagnose disease states. Correlation of the patterns from a plurality of individuals provides an understanding of the mechanisms of disorders or disease states or conditions and in turn provides a rational route to pharmacological development leading to treatment, cure or suppression of such disorders, disease states or conditions.

More particularly, in accordance with the present invention, sample solutions (e.g. body fluids) are electrochemically tested for both normal and abnormal individuals or conditions, patterns are generated for said normal and abnormal individuals or conditions, the patterns compared and differences identified, and the identified differences utilized to design a specific treatment protocol.

In one aspect of the present invention provides a method for developing pharmaceuticals for disorders in living organisms and the pharmaceuticals so produced. The method comprises the steps of analyzing body fluids from normal and afflicted (abnormal) individuals to generate analysis patterns representative of constituents of the metabolic pathways of said individuals; comparing said patterns to determine differences in said patterns representative of (a) the presence or absence of specific compounds in said patterns, or (b) differences in the concentration of said compounds in said patterns; and introducing into a pharmaceutically acceptable carrier therefor one or a mixture of chemical compounds known to act at sites within said metabolic pathways to (a) block or potentiate those metabolic pathways identified as abnormal by the pattern, or (b) supply or retard those unique compounds identified as abnormal in said patterns.

The invention in another aspect provides a method for developing pharmaceuticals for disorders in living organisms and the pharmaceuticals so produced. The method comprises the steps of analyzing body fluids from normal and afflicted (abnormal) individuals to generate analysis patterns representative of individuals' electrochemically active small molecule inventory, comparing said patterns to determine differences in said patterns representative of (a) the presence or absence of specific electrochemically active compounds in said patterns, or (b) differences in the concentration of said compounds in said patterns; and introducing into a pharmaceutical carrier one or a mixture of chemical compounds known to act at sites within metabolic pathways of said organisms to (a) block or potentiate those metabolic pathways identified as abnormal by the pattern, or (b) supply or retard those unique compounds identified as abnormal in said patterns.

The invention also provides a method for identifying pharmacological materials for treating living organisms, which method comprises the steps of analyzing body fluids from normal and afflicted (abnormal) individuals to generate chemical analysis patterns representative of the electrochemically active small molecule inventory contained in said normal and abnormal body fluids; comparing said patterns and identifying differences in said patterns representative of (a) the presence or absence of specific compounds in said patterns, or (b) differences in the concentration of said compounds in the metabolic pathways of said individuals; and selecting from chemical compounds known to act at sites within said metabolic pathways one or a mixture of compounds to (a) block or potentiate those metabolic pathways identified as abnormal by the pattern, or (b) supply or retard those unique compounds identified as abnormal in said patterns.

In yet another aspect the invention provides a method of identifying an abormality in a body fluid of an individual which comprises the steps of determining the presence and relative concentration of electrochemically active compounds contained in said body fluid by passing a sample containing said body fluid sequentially through a liquid chromatographic column for achieving time-space separation of materials eluting from the column and an electrochemical detection apparatus for electrochemically testing a sample containing electrochemically active materials in solution, the detection apparatus comprising a plurality of coulometric cells arranged in series, maintaining the testing electrodes of said coulometric cells at different potentials, said cells operating at progressively varying potentials along the path of flow of the eluant through the cells, and recording the results of coulometric measurements from said cells so as to separate said measurements by measuring potential as well as by time of elution, and comparing the said relative concentrations thus obtained with known concentrations of normal or abnormal body fluids.

Also provided in accordance with the present invention is a method for identifying an abnormality in a body fluid of an individual which comprises the steps of determining the presence and relative concentration of electrochemically active compounds contained in said body fluid by passing a sample containing said body fluid sequentially through a liquid chromatographic column by step gradients for achieving time spaced separation of the materials eluting from the column and an electrochemical detection apparatus for electrochemically testing the eluant from said column, the detection apparatus comprising a plurality of coulometric cells arranged in series, maintaining the coulometric electrodes of said cells at different potentials, said cells operating at progressively varying potentials along the path of flow of the eluant through the cells, recording the results of coulometric measurements from said cells so as to separate said measurements by measuring potential as well by time of elution, and comparing said measurements thus obtained with measurements of normal and abnormal body fluids to provide identification and relevant concentrations of constituents coeluting from the column.

Yet another aspect of the invention provides a method of identifying abnormalities in the small molecule inventory of an individual comprising the steps in sequence of:

determining the presence and relative concentration of electrochemically active constituents in the metabolic pathways containing such abnormalities by passing a sample containing said body fluid sequentially through a liquid chromatograph column for achieving time-space separation of the constituents eluting from the column and an electrochemical detection apparatus comprising a plurality of coulometric cells arranged in series;

maintaining the coulometric electrodes of said cells at different potentials, said cells operating at progressively varying potentials along the path of flow of the eluant through the cells, said plurality of cells being sufficient in number to separate by measuring potentials those relevant constituents coeluted from the chromatographic column at any instant of time and recording the results of such coulometric measurements so as to separate said measurements by measuring potential as well as by time of elution and comparing the said relevant concentrations thus obtained with known concentrations of normal or abnormal body fluids and thereby identify changes of rates through the various metabolic pathways of said relevant constituents as well as unknown metabolites and abnormal precursors for normal metabolites.

The invention also provides a method of determining the relative concentration of principal constituents in the metabolic pathways of an animal by passing a sample containing body fluid from said animal sequentially through a liquid chromatograph column for achieving time-space separation of the constituents eluting from the column and an electrochemical detection apparatus comprising a plurality of coulometric cells arranged in series;

maintaining the coulometric electrodes of said cells at different potentials, said cells operating at progressively varying potentials along the path of flow of the eluant through the cells, said plurality of cells being sufficient in number to separate by measuring potentials those relevant constituents coeluted from the chromatographic column at any instant of time, and recording the results of such coulometric measurements so as to separate said measurements by measuring potential as well as by time of elution.

Also provided in accordance with the present invention is a method for treating a disorder in a living organism which method comprises the steps of analyzing body fluids from normal and afflicted (abnormal) individuals to generate analysis patterns representative of constituents of the metabolic pathways of said individuals; comparing said patterns to determine differences in said patterns representative of (a) the presence or absence of specific compounds in said patterns, or (b) differences in the concentrations of said compounds in said patterns; introducing into a pharmaceutically acceptable carrier therefor one or a mixture of chemical compounds known to act at sites within said metabolic pathways to (a) block or potentiate those metabolic pathways identified as abnormal by the pattern, or (b)

supply or retard those unique compounds identified as abnormal in said patterns; and administering to said living organism said identified compounds in said pharmaceutically acceptable carrier so as to (a) block or potentiate those metabolic pathways identified as abnormal by the pattern, or (b) supply or retard those unique compounds identified as abnormal in said patterns.

Finally, the invention provides a method of treating a disease state in an animal, comprising the steps in sequence of identifying abnormalities in a body fluid of said animal by determining the relative concentration of the principal constituents in the metabolic pathways containing such abnormalities by passing a sample containing said body fluid sequentially through a liquid chromatograph column for achieving time-space separation of the constituents eluting from the column and an electrochemical detection apparatus comprising a plurality of coulometric cells arranged in series;

maintaining the coulometric electrodes of said cells at different potentials, said cells operating at progressively varying potentials along the path of flow of the eluent through the cells, said plurality of cells being sufficient in number to separate by measuring potentials those relevant constituents coeluted from the chromatographic column at any instant of time and recording the results of such coulometric measurements so as to separate said measurements by measuring potential as well as by time of elution and comparing the said relevant concentrations thus obtained with known concentrations of normal or abnormal body fluids and thereby identifying changes of rates through the various metabolic pathways of said relevant constituents as well as unknown metabolites and abnormal precursors for normal metabolites, and identify those compounds responsible for said changes of rates, and administering to said animal said identified compounds so as to provoke a change of rate through said metabolic pathways of said individual substantially to approach that found in said normal fluids.

Yet other objects of the invention will in part appear obvious and will in part appear hereinafter. The invention accordingly comprises the process comprising the several steps and relation of one or more of such steps with respect to each of the others, all of which are exemplified in the following detailed description, and the scope of application as will be indicated in the claims.

For a fuller understanding of the nature and objects of the present invention, reference should be had to the following detailed description taken in combination with the accompanying drawings wherein.

Figure 1:
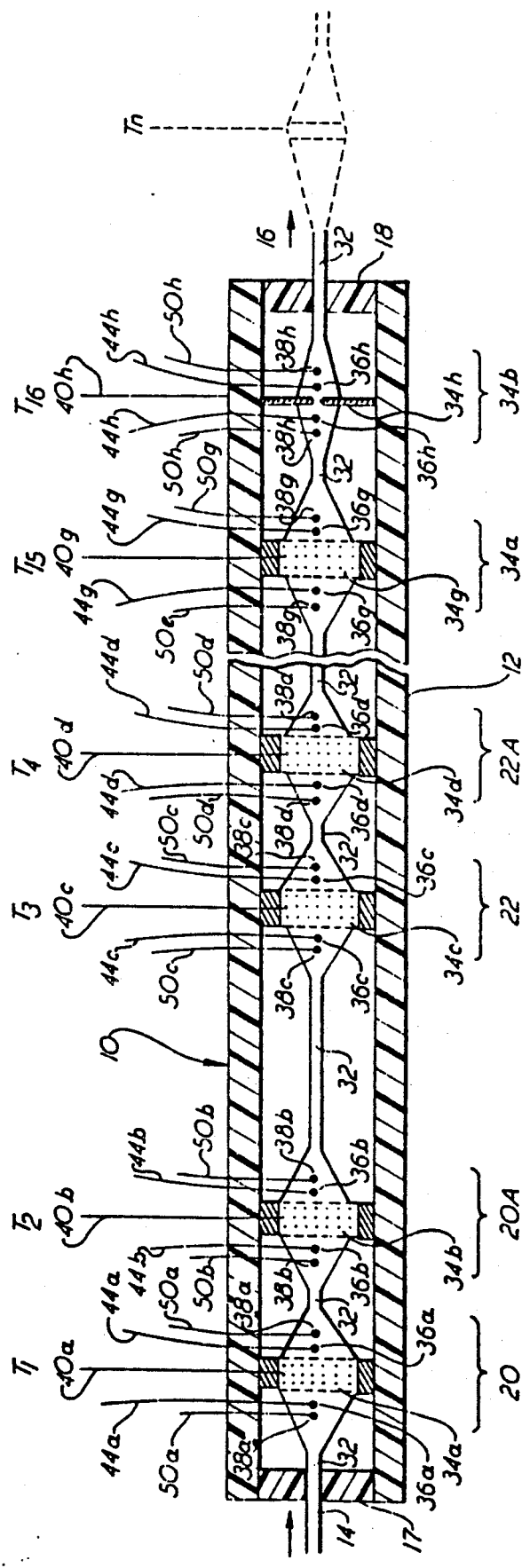
FIG. 1 is a side elevational view, in cross-section, of an electrochemical detection apparatus useful in accordance with the process of the present invention.

Further understanding of the features and objects of the present invention will be had from the following detailed description of one preferred embodiment of the invention which illustrates an electrochemical neurotransmitter pattern generation and resolution and detection of the principal constituents or agents contained in cerebrospinal fluid and affecting motion sickness. It will be understood, however, that the process of the present invention may be advantageously employed for detecting and resolving of various other electroactive metabolites in a biological sample solution, including, but not limited to neurotransmitters, precursors and metabolites, hormones, transmitting compounds, peptides, certain vitamines, pterins, purines, certain drugs and metabolites and other materials that mediate metabolism.

More particularly, the present invention in one aspect provides a method by which sample solutions for both normal and abnormal individuals and conditions are tested, principal constituents or agents resolved and detected, patterns indicating the presence and concentration of such constituents or agents generated, and the differences between the patterns determined whereby compounds suspected of causing said abnormalities or conditions may be identified, and a treatment protocol established through chemical or metabolic therapy, to normalize the (abnormal) pattern, or block or potentiate those metabolic pathways identified as abnormal by the pattern, or supply or retard those unique compounds identified as abnormal in the pattern, or utilize changes in the patterns during therapy and the concentration of the therapeutic drugs and metabolites to modify the course of the therapy.

The first step of the process is to analyze the sample solutions for normal and abnormal individuals or conditions to generate patterns for comparison. The electrochemical detection described in my aforesaid U.S. Pat. No. 4,511,659 is particularly adapted for this purpose. As reported therein such apparatus is capable of responding to and differentiating between electrochemically reversible species in a sample solution and for discriminating against species in a sample solution that are electrochemically irreversible. Sample solutions from normal and abnormal individuals are flowed through a chromatographic column and the eluant is passed through a series of electrochemically isolated cells or "gates" operated at potentials resulting in sequential oxidation and reduction of various species contained in the sample solution. These gates are followed by an array of measuring electrodes for measuring electrochemical activity of compounds of interest. The strategy of analysis discriminates against both background current from the mobile phase itself and removes (screens) compounds that are irreversible, while electrochemically reversible species of interest, e.g. the catecholamines are cycled back and forth from oxidized to reduced state at various potentials whereby to enhance the sensitivity and specificity of downstream detection and measuring electrodes.

For convenience of illustration the function of the gate cells is described as "removing" or "screening" the electrochemically irreversible compounds from the eluant. This is not what actually happens; these compounds are merely electrochemically altered by the gate cells so that the potential existing on the following detecting electrode(s) will not change the oxidation state of the "removed" compound and therefore the "removed" compound will not be detected and coulometrically measured. It is as if the "removed" compound were not present in the eluant. It is no longer electroactive under the detection conditions.

Figure 2:
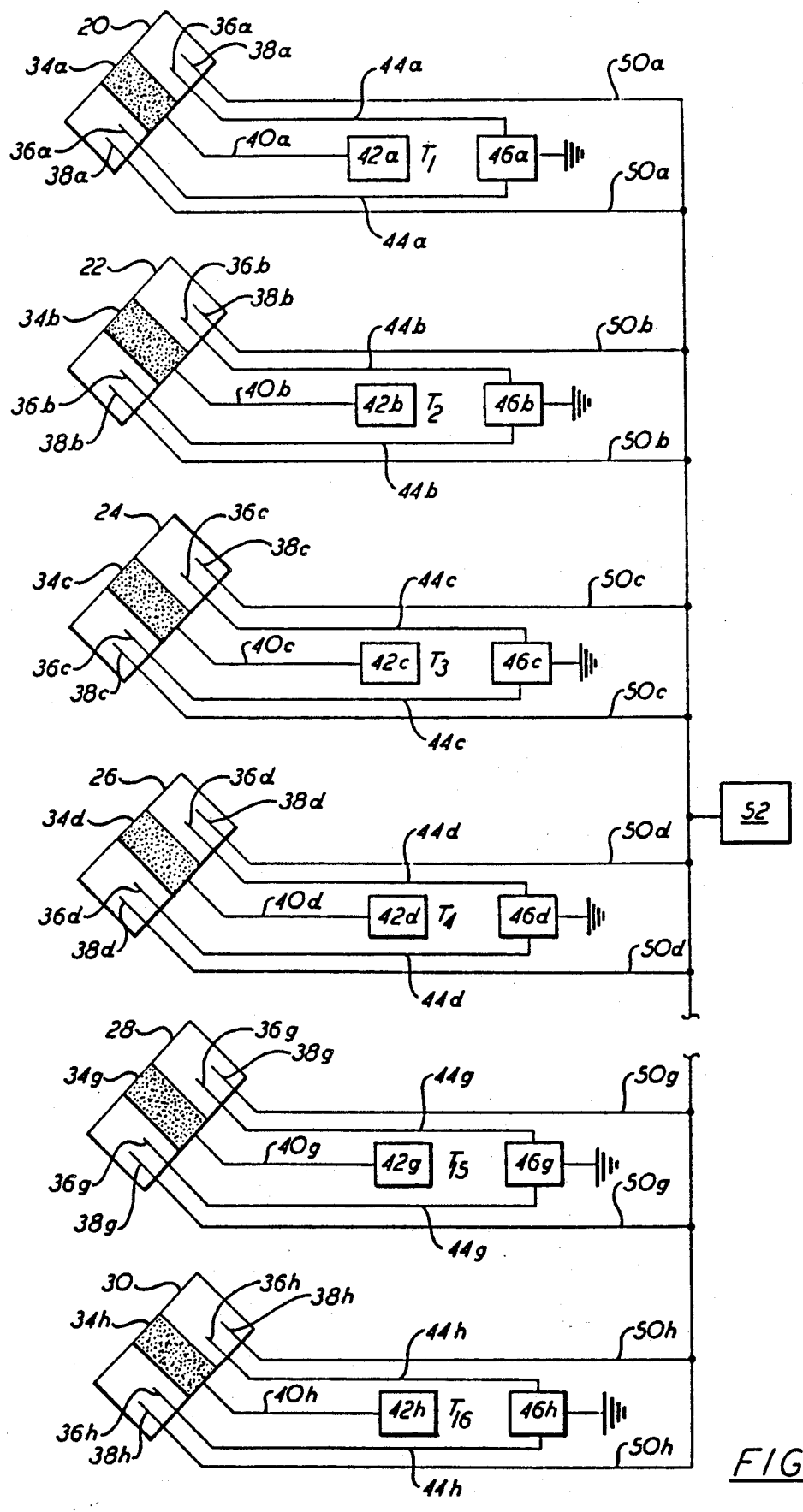
FIG. 2 is a block diagram of the electrical controls and functions of the electrochemical detection apparatus of FIG. 1.
Figure 3A:
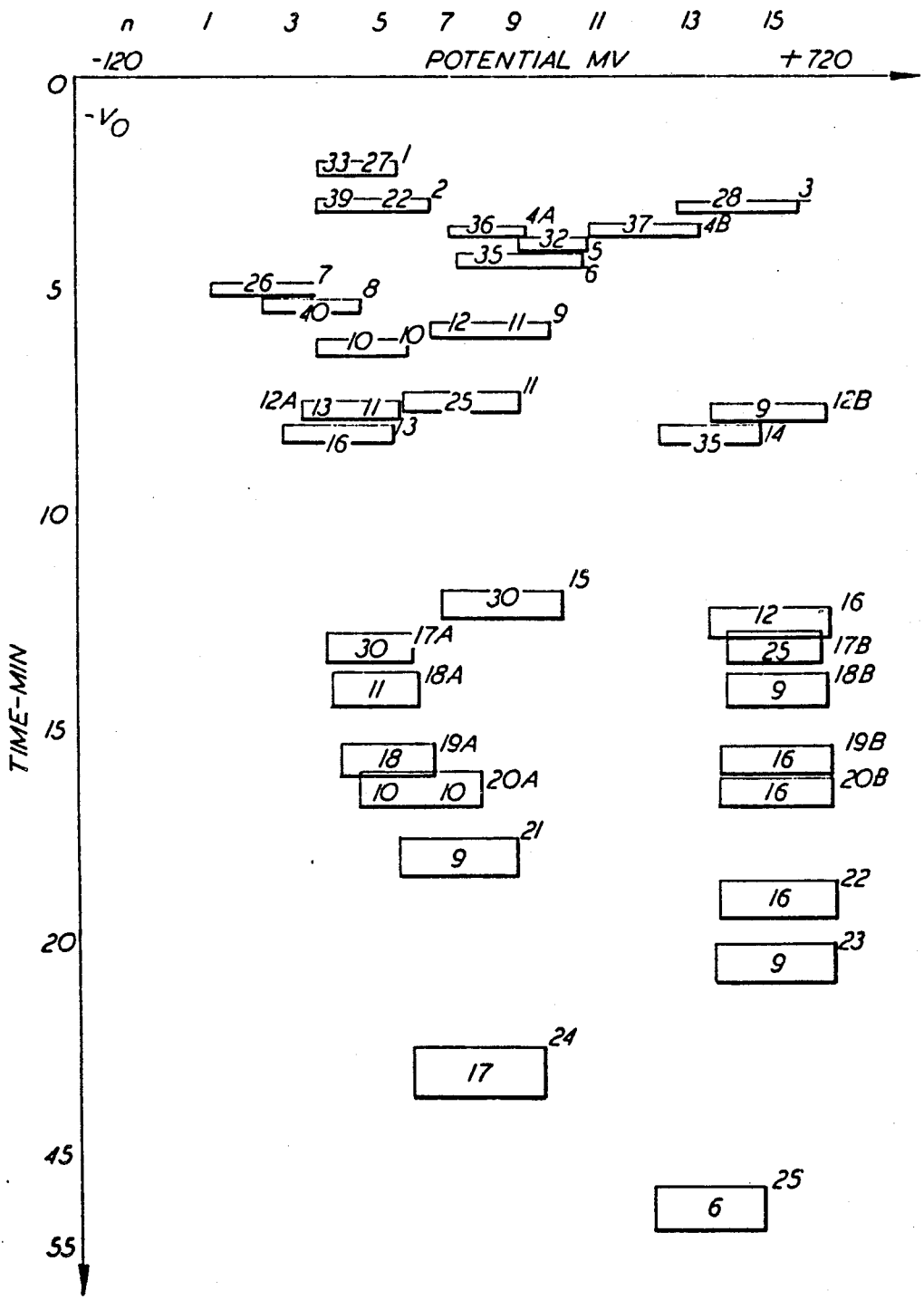
FIGS. 3, 3A & 3B is a time/potential plot of a chromatogram obtained in accordance with the present invention.
Figure 3B:
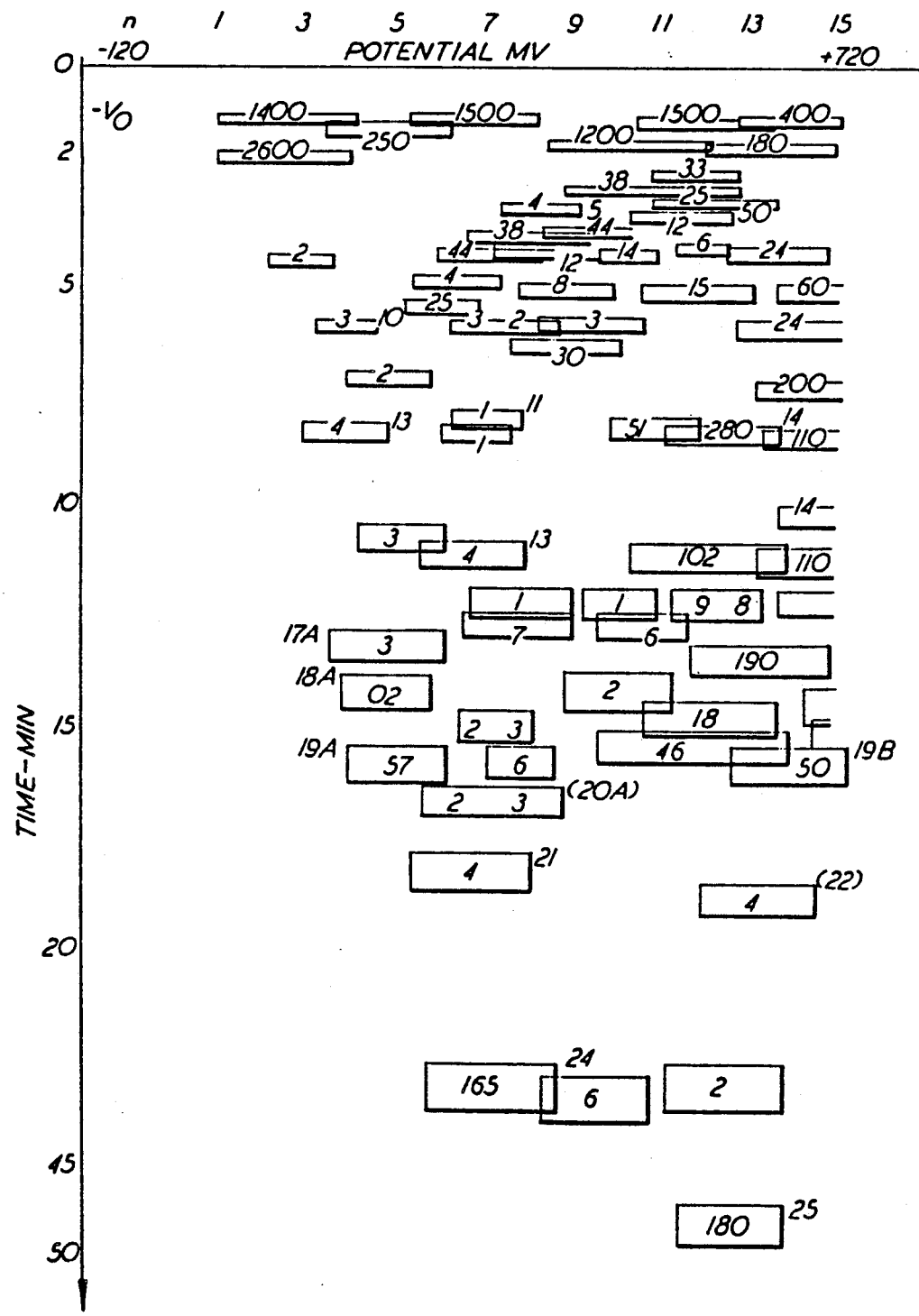
Figure 3:
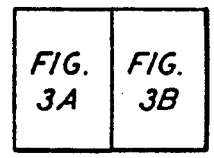

The gate/array cell principal was evaluated using a cell configured typically as shown in FIGS. 1 and 2. In essence, a gate/array cell is designed to set up windows for determination of selected compounds in the catecholaminergic systems and in the indolaminergic system. These assays include Homogenistic Acid (HGA), 3-hydroxy-L-tyrosine (L-DOPA), Norepinephrine (NE), Dihydroxyphenylacetic acid (DOPAC), Epinephrine (EP), Dopamine (DA), 3-Methoxy, 4-Hydroxyphenylglycol (MHPG), and 3-Methoxytyramine (3-MT) to describe the catecholaminegic system, and Tryptophan (TRP), 5-Hydroxytryptophan (5-HTP), 5-Hydroxytryptophal (5-HTOL), Serotonin or 5-Hydroxytryptamine (5-HT), 5-Hydroxy Indole Acetic Acid (5-HIAA), and Homovanillic Acid (HVA) to describe the serotonergic system.

The electrochemical gate/array cell should have a minimum of 8 gates or arrays to effect the desired resolution and preferably will have a minimum of 16 gates or arrays. Preferably the analysis is conducted in three steps. The first step comprises an open array analysis in which the potential on the array is set at relatively wide testing increments. Generally the open array evaluation is performed in two passes, a first pass in which the materials of interest are dissolved in a low organic modifier, e.g. a mobile phase having for example 0 to 1 percent MeOH and $CH_3CN$, and a second pass in which the materials of interest are dissolved in a high organic modifier, typically 30 to 60 percent or more MeOH, and $CH_3CN$ in lower proportions. This provides a first cut. Thereafter, compounds of potential interest based on analysis of the data are evaluated as before, but using a tighter array setting the electrodes to relatively low potential increments over a specific region. As before the analysis is done in two passes—i.e. in a low organic modifier and in a high organic modifier. Finally, selected components then are analyzed under REDOX conditions with oxidation followed by reductive assay. Analyzing the sample in this manner provides extremely high resolution and specificity.

Referring to the details of FIGS. 1 and 2, there is shown a preferred embodiment of the electrochemical detection apparatus useful in accordance with the process of the present invention, indicated generally at 10. Electrochemical detection apparatus 10 comprises a hollow, liquid-tight enclosure indicated generally at 12 and having an inlet 14 and an outlet 16 found in a pair of end plates 17 and 18, respectively. Enclosure 12 is formed of a liquid-impervious, rigid, electrically insulating chemically inert material such as unplasticized polyvinylchloride, polytetrafluoroethylene, fluorohydrocarbon resin or the like. Disposed within enclosure 12 are sixteen electrochemically isolated electrochemical cells 20, 20A, 22, 22A ... 34, 34A. Electrochemical cells 20 ... 34A are hydraulically connected to one another via stub tubing members 32 which together with cells 20 ... 34A define a fluid flow path between inlet 14 and outlet 16. Each electrochemical cell 20 ... 34A comprises a three electrode system consisting of at least one working electrode 34a, 34b, 34c, 34d, 34e, 34g, 34h ($T_1$ ... $T_{16}$) respectively; at least one counter electrode 36a, 36b, 36c, 36d, 36e, 36f, 36g, 36h, respectively; and, at least one reference electrode 38a, 38b, 38c, 38d, 38e, 38f, 38g, 38h, respectively. Electrochemical cells 20 ... 34A are fixedly positioned within enclosure 12 by suitable means (not shown).

Each working electrode 34a ... h ($T_1$ ... $T_{16}$) is in the form of a flat disc formed of a porous electrode base material such as fritted graphite or fritted carbon or other conductive fritted materials. Most of these preferably have a relatively large area to volume ratio to give large half times (up to 90) at the flow rates contemplated and with the electrochemically active materials of interest. Half time is the time required for half of a quantity of a compound to react at an electrode. Allowing a reaction to proceed for two half times causes 75% reaction, 5 half times 97% reaction.

In order to maximize response of the porous working electrodes the electrode base material was pretreated in accordance with the teachings of my copending U.S. Pat. No. 4,976,994 issued Dec. 11, 1990 to load the secondary porosity of the electrode base material with a selected non-electroactive material (i.e. under anticipated sensor conditions) to reduce background noise and enhance selectivity to aminergic compounds. The overall process was as follows: A piece of commercially available fritted graphite was impregnated by a mixture of 80% C-48 paraffin and 20% 0.9163-ML density polyethylene containing 1.00 grams per liter sodium salt of naphthalene sulfonic acid at 110° C. and cycling between vacuum and 1000 psi pressure. Electrodes were cut from the impregnated fritted graphite material and these electrodes were treated to remove the impregnating material blocking the frits by heating at 100° C. for five minutes under a vacuum of 750–760 'mm HgAbs. Thereafter the treated electrode material was rinsed with 50-50 tetrahydrofuran-hexane. The resultant electrode material which contained approximately 0.01% by weight of sorbed napthalene sulfonic acid and approximately one percent by weight of high molecular weight organic material, were assembled in the flow cell detector of a type illustrated in FIG. 1, of my aforesaid U.S. Pat. No. 4,511,659.

Also provided are electrical connections 40a, 40b, 40c, 40d, 40e, 40f, 40g 40h for connecting working electrodes 34a ... h, ($T_1$ ... $T_{16}$) respectively, to potential controls 42a, 42b, 42c, 42d, 42e, 42f, 42g, 42h, respectively, for applying selected working potentials to the various working electrodes 34a ... h; electrical connections 44a, 44b, 44c, 44d, 44e ... 44h, for connecting counter electrodes 36a ... h, respectively, to potential controls 46a, 46b, 46c, 46d, 46e ... 46h ($T_1$ ... $T_{16}$) respectively for applying selected counter potentials to the various counter electrodes; and electrical connections 50b, 50b, 50c, 50d, 50e, 50f, 50g, 50h, respectively, for connecting reference electrodes 38a ... h, respectively to a potential control 52 for applying a reference potential to the various reference electrodes 38a ... h.

Counter electrodes 36a ... h and reference electrodes 38a ... h preferably comprise inert metal terminals such as platinum or palladium wire. Alternatively, reference electrodes 38a ... h may comprise silver/silver chloride reference electrodes or the like. The counter electrodes 36a...h and reference electrodes 38a...h preferably are arranged in pairs to bracket an associated working electrode 34a...h.

In order to minimize or reduce diffusion effects on the counter and reference electrodes, the electroactive surfaces of the metal teminal counter and reference electrodes were coated with a permeable membrane in accordance with the teachings of my copending U.S. Pat. No. 4,976,994 issued Dec. 11, 1990. The overall process was as follows:

Palladium wires were spray coated with Teflon S to build up a coating of approximately 0.0002" thickness. (Teflon S is a trademark of E. I. DuPont de Nemours Company for a synthetic tetrafluorohydrocarbon.) The coated wires thus prepared were dipped sequentially in commercially available Teflon etching solution, concentrated $HNO_3/H_2SO_4$ (50:50 by volume) and tetrahydrofuran in a sonifier bath for approximately 1 minute in each to develop a semipermeable membrane on the wire surface. The Teflon coated/etched palladium wires were cut and assembled as the counter and reference electrodes in accordance with the teachings of my aforesaid U.S. Pat. No. 4,511,659.

As will become clear from the following description electrochemical cells 20...32A act as gate electrodes for discriminating and screening interfering species, while electrochemical array cells 34 and 34A contain the measuring electrodes. In order to achieve high noise discrimination against pressure spikes and voltage fluctuations the measuring electrode should have a relatively small electrode area and thus a relatively small number (e.g. 4) of reaction half-times as compared with the various upstream gate electrodes.

In order to maximize bandspreading and reduce signal-to-noise ratio the electrochemical cell (20...34A) was pretreated to optimize the flow path therethrough in accordance with the teachings of my copending U.S. Pat. No. 4,753,714 issued June 28, 1988. As taught therein, a melted polymer mixture comprising 67 volume percent $C_{48}$ hydrocarbon and 33 volume percent 0.916 density polyethylene, heated to 98° C. was pumped into the cell at 800 psi. Thereafter, water heated to 98° C. was passed through the cell at 0.1 ml/min at 20 psi. The cell was then cooled from 98° C. to ambient (25° C.) over a 15 minute time period by continuing the flow of cooler and cooler water. Thereafter, the cell was flushed at 1 ml/min for 30 minutes with 10/10/80 THF hexane acetonitrile.

Further understanding of the principles and advantages of the present invention may be had by reference to the following examples which are based upon electrochemical analysis employing an electrochemical apparatus made in accordance with FIGS. 1 and 2 and comprising eight electrochemically isolated electrochemical cells 20...34A. The working electrodes 34a...h each comprise fritted graphite discs, treated as above described, each having a working area of approximately 4 $cm^2$ (90 half times). Electrode 34h has a working area of approximately 0.3 $cm^2$ (4 half times). Counter electrodes 36a...h and reference electrodes 38a...h comprise inert metal (palladium) wire terminals treated as above described.

Ccerebrospinal fluid samples from motion-sick, non-sick and motion-sickness resistant cats were analyzed.

The initial hypotheses were:

1. Some compound or compounds are produced within individual animals during motion stimulus that causes the emetic response in susceptible animals; or 2. Some difference in the small molecule inventory or chemical patterns exists in susceptible vs. non-susceptible animals.

Initially, conditions of maximum resolution and sensitivity of known compounds suspected of having a relationship to motion sickness were considered. Thereafter, conditions were defined for maximum resolution of unknown compounds or compounds as appear to be different among sick, non-sick and motion-sickness resistant animals. Cerebrospinal fluid samples were directly injected in a mobile phase comprising 5% MeOH, 2.5% $CH_3CN$ and 0.1M $NaH_2PO_4$ adjusted to pH 3.00 with $H_3PO_4$ and 650 mg/l octane sulfonic acid sodium salt utilizing a Brownlee RP18 3 cm. Guard Column and into a Waters C18μ Bondapak Analytical Column. Mobile phase modifications were carried out for the following samples, under the following operating parameters (all voltage values in millivolts):

REDOX analysis of the samples was performed (oxidation followed by step-wise reduction of the products for detection) under detector conditions chosen for maximum resolution of NE, EP, L-DOPA, DOPAC and DA on $T_1$, HGA on $T_5$ and $T_6$ and indoles on $T_6$, $T_7$ and $T_8$ and the results recorded in Table I.

Detector: $G_C - 350$, $C_C + 400$, $T_1 - 30$, $T_2 - 60$, $T_3 - 140$, $T_4 - 150$, $T_5 - 200$, $T_6 - 230$, $T_7 - 310$, $T_8 - 350$.

TABLE I

| Sample No. | ng/mL in CSF | | | | | |
|---|---|---|---|---|---|---|
| | 2-201* | 2-203 | 2-239* | 2-243 | 2-342 | 2-554 |
| MHPG | 8.20 | 7.10 | 8.00 | 8.80 | 7.60 | 5.30 |
| NE | (LT 0.15) | 0.30 | 0.24 | (LT 0.20) | (LT 0.20) | (LT 0.20) |
| **HGA | 1.02 | 4.80 | 5.30 | 4.40 | 4.80 | 4.40 |
| L-DOPA | 0.66 | 1.10 | 0.90 | 0.89 | 0.89 | 0.67 |
| EP | 1.83 | 2.10 | 1.87 | 2.00 | 1.75 | 1.60 |
| DOPAC | 7.97 | 7.56 | 10.10 | 8.23 | 9.60 | 7.40 |
| DA | (LT 0.38) | (LT 0.30) | (LT 0.30) | (LT 0.30) | (LT 0.30) | (LT 0.30) |
| 5HTOL | 1.07 | 1.25 | 1.30 | 1.21 | 1.65 | 1.14 |
| 5HIAA | 162.00 | 162.00 | 190.00 | 213.00 | 213.00 | 168.00 |
| 5HTP | — | — | — | — | — | — |
| HVA | 116.00 | 112.00 | 131.00 | 125.00 | 135.00 | 109.00 |
| 3MT | (LT 0.90) | (LT 0.90) | (LT 0.90) | (LT 0.90) | (LT 0.90) | (LT 0.90) |
| 5HT | 2.67 | 0.53 | 2.00 | (LT 0.43) | 0.60 | (LT 0.43) |
| T7 + T8 nA** | 5.20 | 44.00 | 74.00 | 41.00 | 45.50 | 41.50 |
| k' = 0.93 | (GT 100) | 24.00 | 7.00 | 8.50 | 4.50 | 3.50 |

TABLE I-continued

| Sample No. | ng/mL in CSF | | | | | |
|---|---|---|---|---|---|---|
| | 2-201* | 2-203 | 2-239* | 2-243 | 2-342 | 2-554 |
| nAT2 k' = 0.93 | 49.00 | 21.00 | (LT 3.00) | 3.00 | (LT 3.00) | (LT 3.00) |
| nAT5 k' = 0.93 | (GT 100) | 47.00 | — | 21.00 | 12.00 | 9.00 |
| nAT6 | | | | | | |

*Average two analysis
**Coelutes with HGA k' = 1.71
LT = less than
GT = greater than Table II shows the result of standards analyzed under these conditions.

TABLE II

| | RESPONSE nA OF STANDARD | | | | | | |
|---|---|---|---|---|---|---|---|
| | 8 | 9 | 10 | X | SD | CV % | |
| T3 + T5 MHPG | 13.8 | 14.2 | 14.4 | 13.86 | 0.332 | 2.40 | 9 |
| T3 NE | 6.0 | 6.2 | 6.2 | 6.04 | 0.133 | 2.21 | 9 |
| T6 HGA | 9.5 | 9.0 | 9.5 | 9.30 | 0.422 | 4.53 | 10 |
| T3 L-DOPA | 10.0 | 10.0 | 9.5 | 9.80 | 0.258 | 2.63 | 10 |
| T3 EP | 4.0 | 3.6 | 3.6 | 3.62 | 0.175 | 4.84 | 10 |
| T3 + TT4 DOPAC | 29.8 | 31.0 | 30.8 | 30.82 | 0.553 | 1.79 | 10 |
| T3 DA | 3.4 | 3.4 | 3.2 | 3.32 | 0.193 | 5.82 | 10 |
| T7 + T8 5HTOL | 18.5 | 18.5 | 17.0 | 14.83 | 0.750 | 5.05 | 6 |
| | | | | 18.37 | 0.250 | 1.33 | 4 |
| T7 + 8 5HIAA | 91.0 | 92.0 | 92.0 | 78.75 | 1.290 | 1.64 | 6 |
| | | | | 91.38 | 0.650 | 0.71 | 4 |
| T3 + T4 HVA | 7.2 | 7.2 | 7.2 | 7.30 | 0.254 | 3.48 | 10 |

In the initial high resolution/selectivity Redox condition several anamolous peaks were noted some of which are listed by their k' and electrode number in Table I. Consequently, a more open 16 channel array from 0 to 1600 millivolts without a gate cell preceding it was utilized to define the more complete structure of profile of the preliminary samples. A series of form mobile phase compositions of increasing organic modifier of 0.5, 5.0, 1.5 and 30% methanol was used. Approximately 300 components were isolated in the various mobile phases. Several of these components appeared to vary as a function of emesis. Qualitative identification of these components was made by comparison of potential/time locations of compounds from Table III.

TABLE III

Partial List of Abbreviations for Chemical Compounds and Typical Ranges Found With Preliminary Gradient Work in Cerebrospinal Fluid (CSF)

| | | ng/mL Typical Values or Range in CSF (Feline ventricular) F F |
|---|---|---|
| Acet | acetaminophen* | — |
| ANA | anthranilic acid NM | |
| ASC | ascorbic acid* | 100–300 |
| BEND | B-endorphin* | |
| THB*DHB | biopterin* | 3–30 |
| BUF | bufotinene* | |
| CAF | caffeic acid* | 0.1–1 |
| CAT | catechol* | 7–17 |
| CCK8 | cholecystokinin 8* | |
| CCK4 | cholecystokinin 4 | + |
| CYSH | cysteine* | |
| DHBAC | 3,4-dihydroxybenzoic acid* | 1–8 |
| DOMA | dihydroxymandelic acid* | 2–6 |
| DOPEG | dihydroxyphenyl glycol* | 0.2–1.0 |
| DHPGA | 3,4-dihydroxyphenyl- glyoxyllic acid | |
| DOPAC | dihydroxyphenylacetic acid* | 8–30 |
| DHQ | 4,8-dihydroxyquinoline* | |
| DMPA | 3,4-dimethoxyphenylacetic acid | |
| DMPEA | 3,4-dimethoxyphenyl- ethylamine | |
| DA | dopamine* | 0.08–0.17 |
| EP | epinephrine* | 0.05–0.32 |
| EPIN | epinine* | + |
| FER | ferulic acid* | + |
| FAN | formylanthranilic acid | |
| FKY | formyl kynurenine* | |
| GA | gentistic acid* | 0.8–2.0 |
| GSH | glutathione* | 50–70 |
| HIST | histamine* | |
| HIS | histidine* | |
| HGA | homogentisic acid* | 0.5–3.0 |
| HQ | hydroquinone | |
| HVA | homovanillic acid* | 50–250 |
| HVOL | homovanillyl alcohol* | 0.5–1 |
| HVRA | homoveratric acid* | |
| HOR | hordenine* | + |
| 3-OHAN | 3-hydroxyanthranilic acid | 0.1–0.2 |
| 5-HIAL | 5-hydroxyindoleacetaldehyde* | |
| 5-HIAA | 5-hydroxyindoleacetic acid* | 150–350 |
| 3OHKYA | 3-hydroxykynurenamine* | |
| 3-OHKY | 3-hydroxykynurenine* | 0.3–1.0 |
| 6-OHMEL | 6-hydroxymelatonin* | |
| 3-HPA | 3-hydroxyphenylacetic acid* | |
| 5-HT | 5-hydroxytryptamine* | 0.1–1.0 |
| 5-HTP | 5-hydroxytryptophan* | 0.2–0.6 |
| 5-HTP-ol | 5-hydroxytryptophol* | 1.5–3.0 |
| I | indole* | |
| IAA | indoleacetic acid* | |
| IET | indole ethanol | |
| IPA | indolepyruvic acid | |
| IS | isatin* | |
| KYA | kynurenic acid* | |
| KYN | kynurenine* | 1.0–2.0 |
| LD | L-dopa* | 0.2–4.0 |
| LENK | leucine enkephalin* | — |
| MEL | melatonin* | |
| MN | metanephrine* | LT 0.01 |
| MENK | methionine enkephalin* | — |
| 5-MGA | 5-methoxygentisic acid | |
| MHMA | 3-methoxy-4-hydroxymandelic acid* | |
| MHPG | 3-methoxy-4-hydroxyphenyl glycol* | 10–40 |
| MHPG-SO4 | MHPG sulfate conjugate* | 100–140 |
| 5-MIAA | 5-methoxyindoleacetic acid* | |

TABLE III-continued

Partial List of Abbreviations for Chemical Compounds and Typical Ranges Found With Preliminary Gradient Work in Cerebrospinal Fluid (CSF)

| | | ng/mL Typical Values or Range in CSF (Feline ventricular) F F |
|---|---|---|
| 3-MT | 3-methoxytyramine* | 0.020 |
| 3-MD | 3-O-methyldopa | |
| MGA | methylgentistic acid* | |
| MHIST | methylhistamine* | |
| mHPA | m-hydroxylphenylacetic acid | |
| mHMA | m-hydroxymandelic acid | |
| mHPPA | m-hydroxyphenylpyruvic acid | |
| mOCT | m-octopamine | |
| mTYRA | m-tyramine* | 1.0–5.0 |
| mTYR | m-tyrosine* | 5.0–10–0 |
| NA5HT | N-acetylserotonin* | 0.5–2.5 |
| NM5-HT | N-methyl-5-hydroxytryptamine* | |
| DM5HI | NN-dimethyl-5-hydroxyindole* | |
| DMTR | NN-dimethyltryptamine | |
| DMTR-P | NN-dimethyltryptamine phosphate | |
| NE | norepinephrine* | 0.2–1.5 |
| NMN | normetanephrine* | LT 0.05 |
| oHTA | o-hydroxyphenylacetic acid | |
| oTYRA | o-tyramine | |
| oTYR | o-tyrosine* | |
| OCT | octopamine* | 0.05–1.5 |
| pCOU | p-coumaric acid* | + |
| pHMA | p-hydroxymandelic acid* | |
| pHPAA | p-hydroxyphenylacetic acid* | 4–10 |
| pHPLA | p-hydroxyphenyllactic acid* | 0–10 |
| pHPPA | p-hydroxyphenylpyruvic acid* | |
| PAC | phenylacetic acid NM | |
| PA | phenylalanine NM | |
| PAE | phenylethylamine NM | |
| PLA | phenyllactic acid NM | |
| PPA | phenylpyruvic acid NM | |
| PAL | pyridoxal* | |
| PALP5 | pyridoxal-5-phosphate* | |
| PYRA | pyridoxamine* | |
| PYRA5P | pyradoxamine-5-phosphate* | |
| PYR | pyridoxine* | + |
| QA | quinaldic acid | |
| SYN | synephrine* | + |
| TRPA | tryptamine* | 1.0–1.8 |
| TRP | tryptophan* | 800 |
| TYRA | tyramine* | 0.5–1.0 |
| TYR | tyrosine* | 1500 |
| U | uric acid* | 600 |
| VA | vanillic acid* | |
| VMA | vanillylmandelic acid* | 0.2–0.3 |

+ indicates observed but not quantified
NM indicates not analyzable by technique
*indicates compound to be included in study
— indicates not present From this work the thirty-nine compounds listed in Table IV were decided upon as candidates for involvement in the emesis event.

Figure 4:
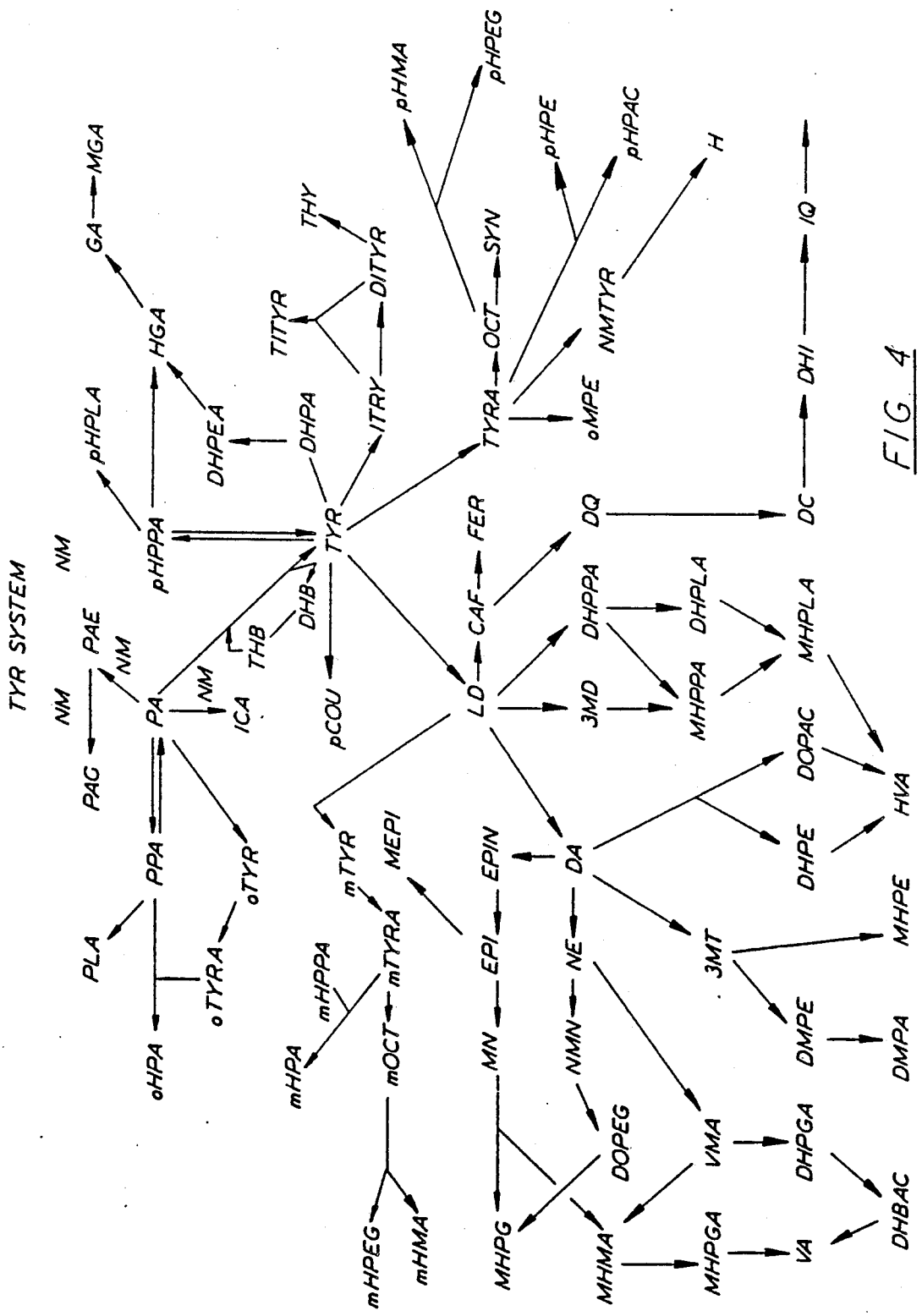
FIG. 4 represents the major metabolic pathways of tyrosine (TYR)
Figure 5:
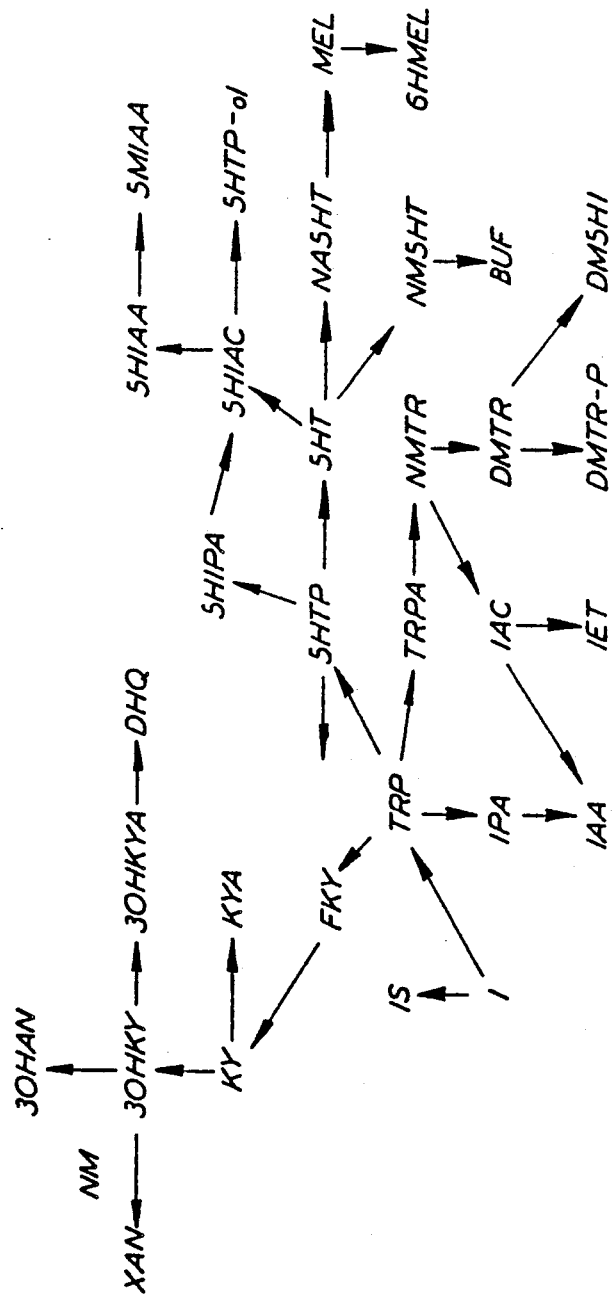
FIG. 5 represents the major metabolic pathways of tryptophan (TRP)

From the preliminary data, one mechanism was postulated for emesis and emesis blocking as a guide to the sample acquisition and analysis protocols to be used in a following study. The mechanism postulated was in the resting cat NE and HGA exist at very low free levels in protein bound pools of approximately 1 and 4 ng/mL, respectively. Stimulus causes the free NE to spike due to neuronal emission. Referring to FIGS. 4 and 5, this emission is mediated by several other neurotransmitter pathways, including the serotonergic and adrenergic and possibly by $B_6$ compounds (which are probable variable peaks in the second array condition). The free NE causes the emesis response and is then deteriorated by adsorption into the bound pool. Free HGA spikes simultaneously either by emission or release from the pool and persists acting as a blocking agent for further emesis from the same stimulus. Several other possible mechanisms could be postulated from the initial data and several other possible abnormalities in the cerebrospinal fluid data were observed in the preliminary study. Among these mechanisms were possible problems associated with the 150 μl sample size acquired. Therefore, in a follow-up study 50–80 μl samples were used and conditions were set up to maximize the total information that could be obtained from a single sample. A step gradient procedure combined with a sixteen channel array cell was utilized to describe the majority of the components of the tyrosine and tryptophan pathways on cerebrospinal fluid samples. Four separate mobile phase solutions were prepared as follows:

Mobile Phase I comprising 0.5 volume percent MeOH, 1 g/l disodium octane sulfonic acid, 0.1M $NaH_2PO_4$ adjusted to pH 3.00 with $H_3PO_4$;

Mobile Phase II comprising 0.5 MeOH, 150 mg/l disodium octane sulfonic acid, 0.1M $NaH_2PO_4$ adjusted to pH 3.00 with $H_3PO_4$;

Mobile Phase II comprising 1.0 volume percent isopropanol alcohol, 0.5 volume percent MeOH, 175 mg/l disodium octane sulfonic acid, 0.1M $NaH_2PO_4$ adjusted to pH 3.00 with $H_3PO_4$; and Mobile Phase IV comprising 5 volume percent isopropanol alcohol, 0.5 volume percent MeOH, 275 mg/l disodium octane sulfonic acid, 0.1M $NaH_2PO_4$ adjusted to pH 3.00 with $H_3PO_4$.

Figure 9:
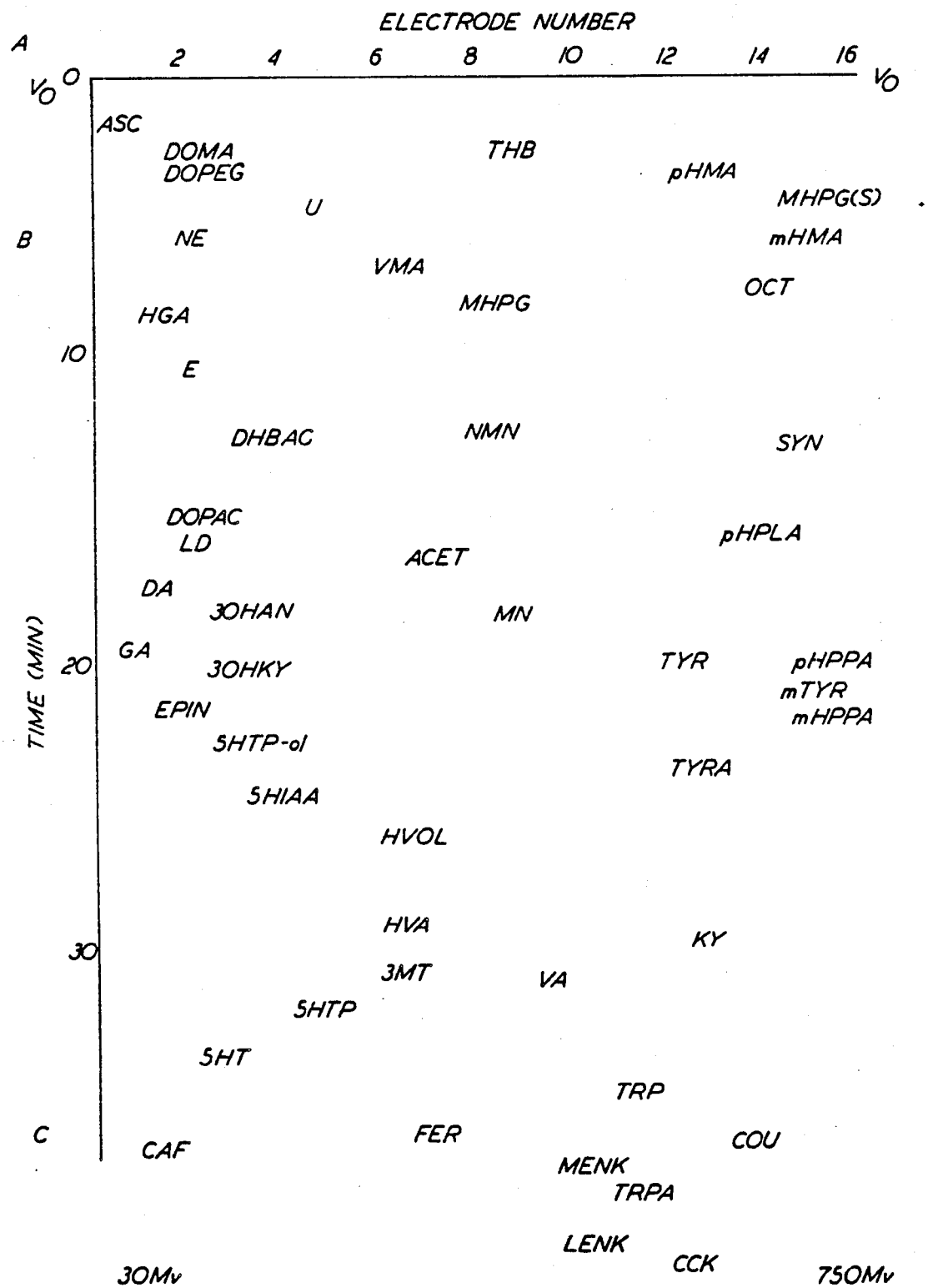
FIG. 9 is a voltage/time resolution pattern obtained in accordance with the present invention.

The overall procedure is as follows:

First the column was swept with Mobile Phase IV. Mobile Phase I was then flowed through the column for one minute. 200 microliters comprising a mixture of 1.0 mg/ml ascorbic acid and 0.5 mg/ml EDTA was injected into the column and Mobile Phase I was flowed through the column for an additional five minutes. At the six minute mark, the mobile phase was changed to Mobile Phase II and flow continued for an additional eighteen minutes. Sample solution was injected into the column at the 24 minute mark. At the 35 minute mark the mobile phase was shifted to Mobile Phase III and at the 60 minute mark the mobile phase was shifted to Mobile Phase IV. Mobile phase flow was continued for twenty-five minutes, the mobile phase was then shifted back to Mobile Phase I and the sequence repeated with additional samples. A typical voltage/time resolution pattern for this method is shown in FIG. 9.

A double blind analysis of 106 samples from emesis susceptible, emesis moderately susceptible and emesis non-susceptible animals was performed. Thirty-nine components under controlled test were analyzed in each sample and separated from 150 additional unknown components utilizing the electrochemical imaging system of the present invention. Column temperature was maintained at 23.5° C. plus or minus 0.1° C. The results of the precision of the method as derived from coanalyzed standard is shown in Table IV. Of the thirty-nine components, approximately thirty were present and unambiguously identified in all samples and submitted to extensive statistical analysis.

TABLE IV

| Compound | C CV |
|---|---|
| DHPAA | 4.1 |
| MHPG-SO$_4$ | 7.4 |
| THB | 4.3 |
| DOMA | 6.16 |
| DOPEG | 4.81 |

TABLE IV-continued

| Compound | C CV |
|---|---|
| pHMA | 2.37 |
| U | 2.32 |
| NE | 4.60 |
| VMA | 5.37 |
| MHMA | 8.23 |
| MHPG | 3.71 |
| OCT | 6.2 |
| HGA | 8.3 |
| EP | 5.43 |
| DHBAC | 2.91 |
| NM | 3.80 |
| LD | 6.31 |
| DOPAC | 5.21 |
| SYN | 10.4 |
| GA | 4.31 |
| pHPLA | 6.21 |
| 3-OHAN | 9.85 |
| DA | 7.62 |
| 3-OHKY | 7.95 |
| TYR | 6.34 |
| pHPAC | 6.12 |
| mTYR | 6.01 |
| MN | 5.72 |
| 5HT-Ol | 6.71 |
| EPIN | 5.71 |
| TYRA | 6.84 |
| 5-HIAA | 3.74 |
| HVOL | 4.80 |
| HVA,VA | 3.01 |
| 5-HTP | 4.54 |
| 3-MT | 6.12 |
| 5HT | 4.03 |
| CAF | 5.12 |
| TRP | 5.01 |

The potential/time locations of the analytes in the tyrosine (TYR) and tryptophan (TRP) metabolic pathways (FIGS. 4 and 5) were plotted on X-and-Y time and potential axes as shown in FIG. 9. Individual analytical values were obtained by comparison of the magnitude of a standard at the XY locations for the samples. From the data produced on 106 samples for 28 compounds, significant differences between emesis susceptible and emesis non-susceptible individual animals were found in the Noradrenergic, Dopaminergic, Serotonergic and Purine metabolic systems. The compounds quantitated reflect the various pathways affecting the Dopamine metabolites and others. These values were considered in terms of an algorithm to reflect the possible concentrations of MHPLA (3-methoxy-4-hydroxy phenyl lactic acid) to the HVA concentration, 3-MT to increasing the DOPAC concentration, and DHPE (dihydroxyphenyl ethanol) and MHPE or HVOL (3-methoxy-4-hydroxyphenyl ethanol) to decreasing the DOPAC concentration:

From this information an appropriate compound to block the motion induced emesis was deduced, and the compound was successfully tested on moderately emesis susceptible animals.

It can be seen the present invention permits determination of the precise identity of causative agents, e.g. neurotransmitters responsible for motion-sickness, and allows the manipulation of metabolic pathways which appear to have the effect of blocking motion sickness. Determination of the precise identity of these compounds provides a valuable adjunct both to the diagnosis of the causative conditions or syndromes leading to a disorder, and also can provide the physician, veterinarian or pharmacologist with an analysis tool for describing essentially the complete small molecule or substance inventory of an individual or group of individuals, essentially the entire complex metabolic pathways of such substances, and the identity of naturally occurring substances or chemical adjuncts for treating a disorder or related diseases. This permits, for example, those compounds identified as blocking agents, or precursors of said blocking agents, to be administered directly to an individual, or dietary modification which will cause the individual to produce internally the desired blocking agents may be administered. This also permits the exact definition of differences in metabolic pathways between classes of individuals and allows the selected administration of compounds which enhance or retard the appropriate segment of the metabolic system. This provides a key to the rational identification, development, manufacture and/or administration of existing or new pharmacological drugs and treatment protocols. Thus, in order to treat a disorder resulting from a diagnosed chemical imbalance such as a neurological disorder the physician or veterinarian need merely administer to the patient sufficient blocking agents, substances, or precursors thereof to make up for a deficiency in the naturally occurring blocking agent or substance or administer the appropriate metabolic inhibiting substance to modify the metabolic pathways described using the chemical imaging system above described. Moreover, the ability to determine the precise chemical nature of a neurological disorder, e.g. in comparison with a normal individual, is an extremely important and desirable test, and may permit early identification and classification of individual disorders, and a treatment protocol with those naturally occurring compounds, substances or precursors which have a specificity for blocking, mediating or otherwise eliminating the disorder.

In other words, the present invention permits normalizing information from precursors and metabolites of the neurotransmitters or other chemicals identified as active in disorders such that algorithms for the compounds measured can be developed. These algorithms can be utilized to compensate for biological variability in individuals, products and metabolism and refine the assessment of the effect of an individual neurotransmitter or pathway. Thus in the emesis case entire metabolic pathways when considered as a whole were shown to be different between susceptible and non-susceptible individuals, intervention guided by the chemical imaging pathway definition to make the susceptible pathways approach the non-susceptible was efficatious in suppressing emesis. It should also be recognized that the patterns obtained may show specific presence or absence of compounds in a particular disease state. For example, as discussed in my aforesaid U.S. Pat. No. 4,511,659, a significant binary different between cerebrospinal fluid samples from patients with dementia of the Alzheimer type and normals was found in the apparent oxidation states of the neurotransmitters serotinin or 5-hydroxy tryptamine (5HT), and its precursor 5-hydroxy tryptophan (5HTP). Assuming these compounds to have causative effect in Alzheimers, by blocking the generation of these compounds through metabolic pathways, the potential toxic effects of such compounds may be mediated or eliminated. Having identified those specific compounds which appear to reflect an underlying condition, one skilled in the art rationally may determine the point in the metabolic pathway in which to intervene in order to eliminate or block the generation of potentially toxic materials.

Blocking agents have an established and valued place in symptomatic treatment of various allergic reactions or disease. The present invention is based in part on the realization that there are certain naturally occurring blocking agents in living organisms. In certain instances disease or disorder is caused by an imbalance or insufficiency of blocking agents. In other instances such as stress, e.g. due to motion sickness, blocking agent production may be insufficient, or simply too slow to produce the desired blocking effect from the initial insult. The present invention in part provides a method for identifying those individuals susceptible to a particular disorder, and those particular blocking agents or precursors thereof, or other substances or compounds, which advantageously may be administered to that individual whereby to enhance or retard an appropriate segment of that individual's metabolic pathway. Thus, for example, while classical blocking drugs are pharmacological antagonists that appear to act by occupying receptors on the effector cell, to the exclusion of agonist molecules without themselves initiating a response, blocking agents identified in accordance with the present invention necessarily need not react in a similar manner. The important criteria is that the so-called blocking agent or other substance employed in therapy produces in the individual a normalized or near normalized reaction.

Unlike artificial drugs the blocking agents or other substances or compounds identified in accordance with the present invention are naturally occurring in the body of the individuals. Accordingly the usual side effects, contraindications, etc. as normally may be experienced with administration of artificial drugs may not result in administration of blocking agents or other substances or compounds identified in accordance with the present invention.

One skilled in the art will recognize the aforesaid invention is susceptible to modification. Thus, for example, while the electrochemical apparatus has been illustrated as having sixteen electrochemically isolated gate-/array cells, any number of electrochemically isolated electrochemical-gate/array cells may be employed in series to achieve the desired results. Moreover, reaction half-times may be modified by manipulating individual cell volumes which in turn may reduce certain kinds of noise. Also, two or more sensing electrode cells may be employed downstream of one another to detect and measure additional groups of compounds of interest. For example, after a four-electrode gate sequence to eliminate irreversible substances and define the upper and lower potential limits, an array of sensors (for example 10 to 16), if desired, including also additional gate electrodes, could be arranged in an increasing oxidative and then reductive modes. This will effectively display the current voltage curves for eluting compounds for both their oxidative and reductive modes. The current from each electrode will produce one set of simultaneous equations as follows:

$$i = A(C_a) + B(C_b) = C(C_c) \qquad \text{I.}$$

where A, B and C are constants defined by the potential and the nature of the compounds a, b and c and where $C_a$, $C_b$, $C_c$, . . . are the concentrations of a, b and c. It would then be possible to solve and display, for as many coeluting components as there are sensors in the array, providing that there is not an absolute identity in the signature or current voltage curve. Employing an array of sensors in sequence would enhance sensitivity of the cells, and also enhance separation of compounds that co-elute.

Figure 6:
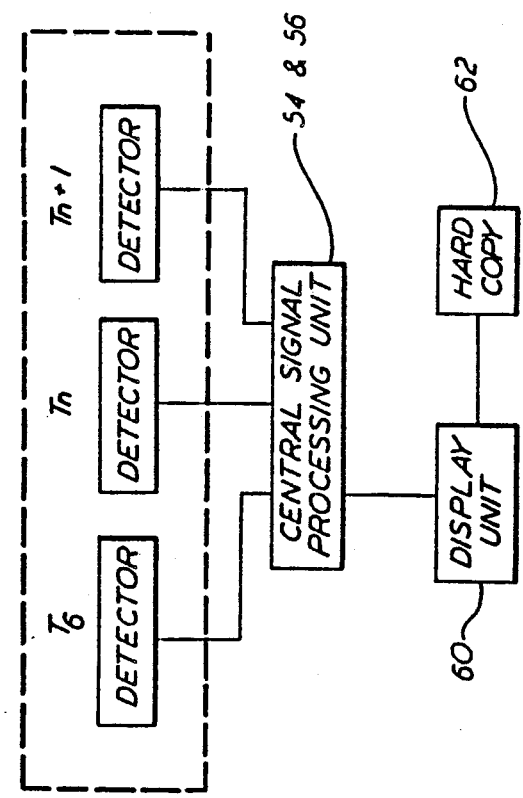
FIG. 6 is a schematic diagrammatic drawing of a detection system useful in accordance with the process of the present invention wherein a plurality of test (or measuring) cells are employed after the gate cells and the outputs of the test cells are processed by a central processing unit.

FIG. 6 is a block diagram of a system for processing such dual signals. The elements illustrated in FIG. 6 are given the same numbers as the equivalent elements in FIGS. 7 and 8.

Through the use of peak signatures, there have been detected in the analysis of cerebrospinal fluid and brain tissue several peaks whose "signatures" were clearly not identical to that of the standard compound normally observed at that retention time. Prior art detection methods would not have allowed for the resolution of such co-eluting compounds and would have resulted in erroneous data. This new technology has clearly provided a much needed method for determining the existence of co-eluting compounds and has virtually eliminated the misidentification of neutrotransmitters.

Additionally, two-dimensional pattern diagrams, i.e. electrochemical fingerprints of various selected materials, can be generated, similar to two-dimensional pattern diagrams achieved by standard chromatography techniques by suitably integrating signals on various electrodes. In such case, samples of known substances may be flowed through the electrochemical apparatus, and two-dimensional pattern diagrams in the form of voltammograms representing the selected substances generated using the apparatus and procedures above described. The resulting pattern diagrams may be stored in a suitable central processing unit for subsequent pattern matching and identification.

The process thus described also may be advantageously employed for directly analyzing body fluids such as urine or blood for the purpose of diagnosing diseases or predisposition to diseases of a subject and establishing pharmaceutical protocols (sequence, type and concentration of pharmaceuticals) for treating such diseases, thus providing unexpected and marked advantages over the many step chromatographic analysis techniques reported by A. B. Robinson and L. Cauling, in the paper entitled "Techniques of Ortho-Molecular Diagnosis" in *Clinical Chemistry*, Vol. 20, No. 8, 1974, pages 967–965, and by Miyagi et al, in U.S. Pat. No. 4,338,811.

Figure 7:
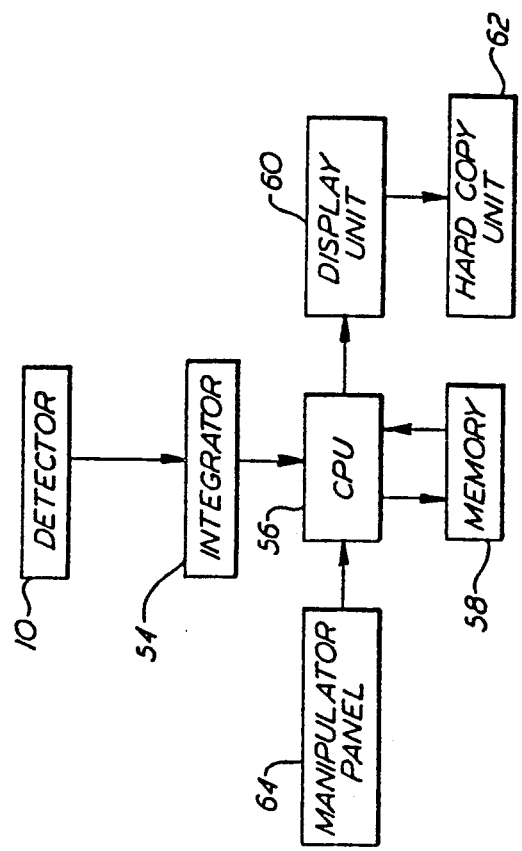
FIG. 7 is a flow chart of an embodiment of disease detection and treatment design method according to the present invention.
Figure 8:
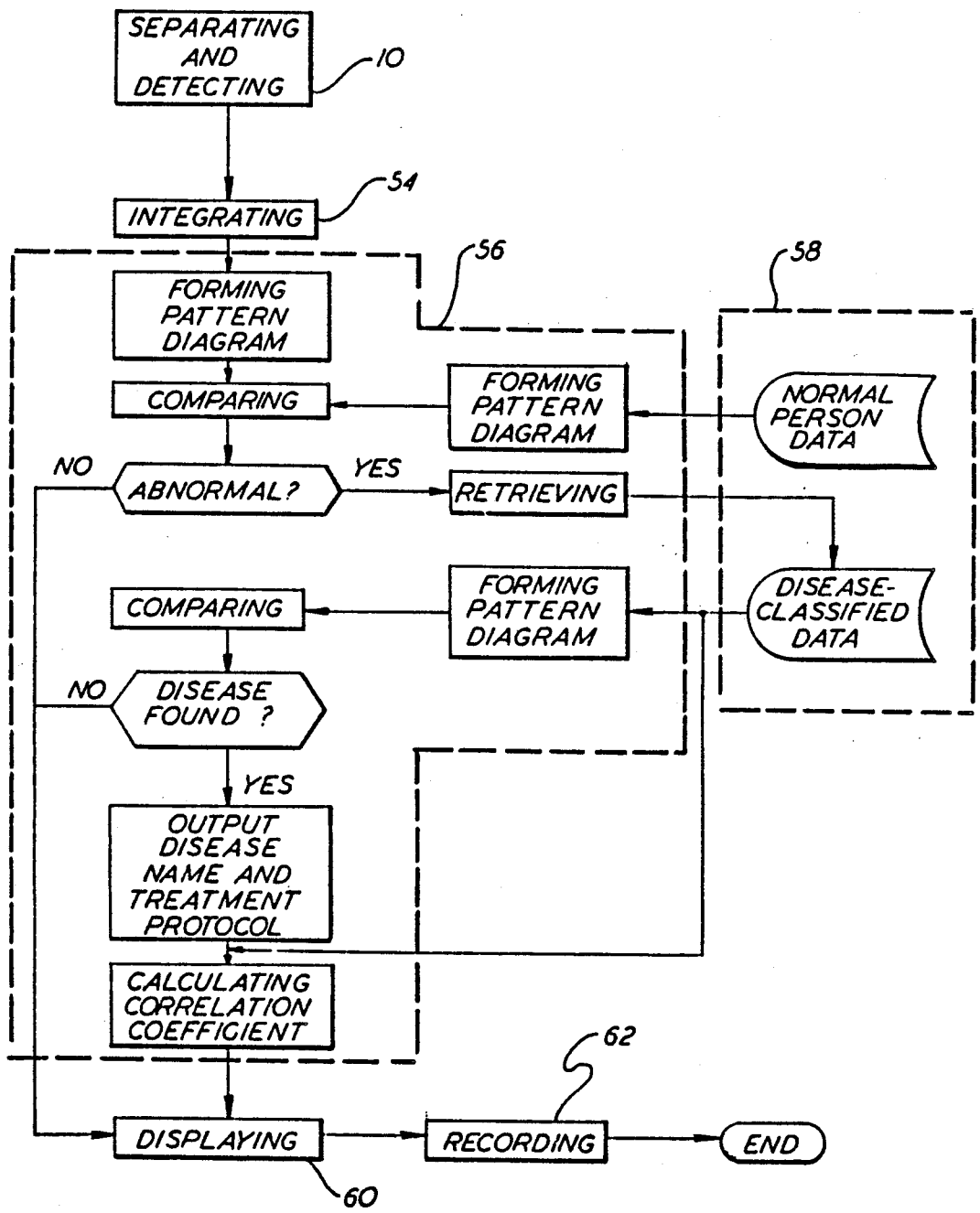
FIG. 8 is a block diagram of an electrochemical apparatus adapted for the practice of the method shown in FIG. 7.

Referring to FIGS. 7 and 8, a sample fluid may be directly streamed into the electrochemical detection apparatus 10 as described in detail supra, where substances of interest may be separated and detected in the manner previously described. Individual peaks in the output signal from the detector 10 may then be integrated in an integrator 54, and the output signal from the integrator 54 applied to a central processing unit 56 which is referred to as a CPU hereinafter as described by Mijagi et al. In the CPU 56, a two-dimensional pattern diagram representing the relation between the peak areas and the retention times provided by the input signal is formed according to a preset program. When peak matching (shown in FIG. 7) is required, a reference chromatogram is read out from a memory 58 such as a magnetic tape or a magnetic disk, and the two dimensional pattern diagram above described is formed after the CPU 56 judges whether or not the retention time of each peak in the subject's chromatogram coincides with the retention time of the corresponding peak in the reference chromatogram and carries out peak matching when coincidence is not detected.

Then, the data of the upper and lower limits of normal persons are read out from the memory 58 upper limit pattern diagram and lower limit pattern diagram of the normal persons in the CPU 56. The pattern diagram of the data of the subject is then compared geographically with these upper and lower limit pattern diagrams in the CPU 56 so as to judge whether the subject is normal or abnormal. The result of judgment is displayed on a display unit 60 and recorded by a hard copy unit 62. As described hereinbefore, the process of the comparison and judgment may be displayed when so desired.

As shown in FIG. 8, the process of disease diagnosis is completed when the subject is judged to be normal. When, on the other hand, the subject is judged to be abnormal, the CPU 56 retrieves disease data in a manner as described hereinbefore from the file of classified diseases stored in the memory 58. On the basis of the thus retrieved disease data, the CPU 56 forms the upper limit pattern diagram and lower limit pattern diagram of the disease and compares geographically these pattern diagrams with the subject's pattern diagram so as to select the corresponding disease or analogous disease. Further the CPU 56 calculates the correlation coefficient between the pattern diagram of the subject and the average-valve curve of the selected disease and identifies the chemical deficiency of the subject, and thus a treatment protocol. The result of selection of the corresponding disease or analogous disease, the result of calculation of the correlation coefficient and/or the process of disease diagnosis by comparison of the pattern diagrams, and the treatment protocol, are displayed on the display unit 60 and recorded by the hard copy unit 62. When it is necessary to modify some of the data on the basis of doctor's other observations in the course of judgment of the normality or abnormality or in the course of disease selection, necessary data are applied from a manipulator panel 64 to the CPU 56 for the purpose of modification of the data.

The invention has been described for use in analyzing Tyrosine and Tryptophan derived neurotransmitters, precursors and metabolites vis-a-vis their role in motion-induced emesis. It will be understood, however, that the invention advantageously may be used to diagonose and characterized disorders, and to characterize and establish pharmaceutical protocols for a variety of environmentally induced, inherited and/or degenerative disorders such as Alzheimer's Disease, Parkinson's Disease, Huntington's Disease, ALS, MS and senile dementias; behavioral disorders such as depression, suicide, hyperactivity, weight control, schizophrenia, learning disabilities, memory retention, alcohol and substance abuse and dependency and sleeplessness; emesis in pregnancy or following chemotherapy; post operative anesthesia response; and hypertension and cardiovascular involvement which are given as exemplary. One skilled in the art will recognize that the apparatus and method above-described advantageously may be employed for resolving mixtures of a large number of electroactive organic substances among which are mentioned unsaturated hydrocarbons, azides, triazines and phenothiazines, amino acids, amines and amides, phenols, aromatic OH, quinolines, quinones, imines, olefins, ketones, aldehydes, esters, olefinic esters, ethers, organometallics, diazo compounds, nitro compounds, and halogens. Electroactive organometallic compounds in association with macro molecules also can be resolved using the electrochemical apparatus and method above desired.

Still other changes and advantages will be obvious to one skilled in the art.

I claim:

1. A method for developing a treatment protocol for correcting an abnormal condition or disease in a living organism which method comprises the steps of:

supplying body fluids that contain electrochemically active constituents which are representative of the metabolic pathways of normal and abnormal or diseased individuals of the living organism;

analyzing the samples to detect the individual electrochemically active constituents representative of the metabolic pathways of said individuals by passing a sample containing body fluid from said living organism sequentially through (a) a liquid chromatograph column for achieving time-space separation of the constituents eluting from the column and (b) an electrochemical detection apparatus comprising a plurality of coulometric cells arranged in series;

maintaining the coulometric electrodes of said cells at different potentials, said cells operating at progressively varying potentials along the path of flow of eluant through the cells, said plurality of cells being sufficient in number to separate by measuring potentials of those relevant electrochemically active constituents coeluted from the chromatographic column at any instant of time, and recording the results of such coulometric measurements so as to separate said measurements by measuring potential as well as time of elution;

comparing the representative electrochemically active constituents concentrations thus obtained with representative electrochemically active constituent concentrations of other living organisms and thereby identifying any differences between the various metabolic pathways of said representative electrochemically active constituents as well as unknown metabolites;

identifying those compounds which effect the presence and concentration of the representative electrochemically active constituents of the metabolic pathways; and administering to said organism said compounds which provoke a change in said metabolic pathways and representative electrochemically active constituents substantially to approach that found in body fluids of normal organisms.

2. A method according to claim 1, wherein said body fluid contains a blocking agent, and including the step of adjusting the metabolic pathways by administering a measured quantity of said blocking agent to said living organism.

3. A method according to claim 2, and including the step of provoking a change in the metabolic pathways of said living organism by administering a chemical compound which promotes autogenetic production of said blocking agent in said living organism.

4. A method according to claim 1, wherein said body fluid comprises serum.

5. A method according to claim 1, wherein said body fluid comprises cerebrospinal fluid.

6. A method according to claim 1, wherein said body fluid comprises plasma.

7. A method according to claim 1, wherein said body fluid comprises urine.

8. A method according to claim 1, wherein said body fluid comprises saliva.

9. A method according to claim 1, wherein said tissue comprises brain tissue.

10. A method for selecting a pharmaceutical for treating abnormal or diseased living organisms which method comprises the steps of:

supplying body fluids that contain electrochemically active constituents which are representative of the metabolic pathways of normal and abnormal or diseased individuals of the living organism;

analyzing the samples to detect the individual electrochemically active constituents representative of the metabolic pathways of said individuals by passing a sample containing body fluid from said living organism sequentially through (a) a liquid chromatograph column for achieving time-space separating of the constituents eluting from the column and (b) an electrochemical detection apparatus comprising a plurality of coulometric cells arranged in series;

maintaining the coulometric electrodes of said cells at different potentials, said cells operating at progressively varying potentials along the path of flow of eluant through the cells, said plurality of cells being sufficient in number to separate by measuring potentials of those relevant electrochemically active constituents coeluted from the chromatographic column at any instant of time, and recording the results of such coulometric measurements so as to separate said measurements by measuring potentials as well as time of elution;

comparing the representative electrochemically active constituent concentrations thus obtained with representative electrochemically active constituent concentrations of other living organisms and thereby identifying any differences between the various metabolic pathways of said representative electrochemically active constituents as well as unknown metabolites;

identifying those compounds which effect the presence and concentration of the representative electrochemically active constituents of the metabolic pathways; and selecting one or a mixture of chemical compounds known to (a) block or potentiate selected metabolic pathways identified by the analysis, or (b) supply or retard selected molecules within said metabolic pathway.

11. A method according to claim 10, wherein said sample contains an electrochemically active blocking agent, and including the step of electrochemically examining said sample to identify said blocking agent.

12. A method according to claim 10, wherein said body fluid comprises serum.

13. A method according to claim 10, wherein said body fluid comprises cerebrospinal fluid.

14. A method according to claim 10, wherein said body fluid comprises plasma.

15. A method according to claim 10, wherein said body fluid comprises urine.

16. A method according to claim 10, wherein said body fluid comprises saliva.

17. A method according to claim 10, wherein said body fluid is derived from a body tissue.

18. A method for identifying pharmaceutically active compounds for testing living organisms for correcting an abnormal condition or disease, which method comprises the steps of:

supplying body fluids that contain electrochemically active constituents which are representative of the metabolic pathways of normal and abnormal or diseased individuals of the living organism;

analyzing the samples to detect the individual electrochemically active constituents representative of the metabolic pathways of said individuals by passing a sample containing body fluid from said living organism sequentially through (a) a liquid chromatograph column for achieving time-space separation of the constituents eluting from the column and (b) an electrochemical detection apparatus comprising a plurality of coulometric cells arranged in series;

maintaining the coulometric electrodes of said cells at different potentials, said cells operating at progressively varying potentials along the path of flow of eluant through the cells, said plurality of cells being sufficient in number to separate by measuring potentials of those relevant electrochemically active constituents coeluted from the chromatographic column at any instant of time, and recording the results of such coulometric measurements so as to separate said measurements by measuring potential as well as time of elution;

comparing the representative electrochemically active constituent concentrations thus obtained with representative electrochemically active constituent concentrations of other living organisms and thereby identifying any differences between the various metabolic pathways of said representative electrochemically active constituents as well as unknown metabolites;

identifying those compounds which effect the presence and concentration of the representative electrochemically active constituents of the metabolic pathways; and selecting one or a mixture of chemical compounds known to (a) block or potentiate selected metabolic pathways identified by the analysis, or (b) supply or retard selected molecules within said metabolic pathway.

19. A method according to claim 18, wherein said body fluid comprises a fluid selected from the group consisting of serum, cerebrospinal fluid, plasma, urine and saliva.

20. A method according to claim 18 wherein said body fluid derives from a body tissue.

21. A method according to claim 20 wherein said body tissue comprises brain tissue.

22. A method for treating an abnormal condition or disease in a living organism which method comprises the steps of:

supplying body fluids that contain electrochemically active constituents which are representative of the metabolic pathways of normal and abnormal or diseased individuals of the living organism;

analyzing the samples to detect the individual electrochemically active constituents representative of the metabolic pathways of said individuals by passing a sample containing body fluid from said living organism sequentially through (a) a liquid chromatograph column for achieving time-space separation of the constituents eluting from the column and (b) an electrochemical detection apparatus comprising a plurality of coulometric cells arranged in series;

maintaining the coulometric electrodes of said cells at different potentials, said cells operating at progressively varying potentials along the path of flow of eluant through the cells, said plurality of cells being sufficient in number to separate by measuring potentials of those relevant electrochemically active constituents coeluted from the chromatographic column at any instant of time, and recording the results of such coulometric measurements so as to separate said measurements by measuring potential as well as time of elution;

comparing the recorded results thus obtained with representative electrochemically active constituent concentrations of other living organisms and thereby identifying any differences between the various metabolic pathways of said representative electrochemically active constituents as well as unknown metabolites;

identifying those compounds which effect the presence and concentration of the representative electrochemically active constituents of the metabolic pathways;

selecting one or a mixture of chemical compounds known to (a) block or potentiate selected metabolic pathways identified by the analysis, or (b) supply or retard selected molecules within said metabolic pathways and introducing said compounds into a pharmaceutically acceptable carrier; and administering to said living organism a pharmaceutically effective amount of said selected chemical compounds in said pharmaceutically acceptable carrier.

23. A method for treating a disease state in an animal which method comprises the steps of analyzing body fluid between animals by:

supplying body fluids that contain electrochemically active constituents which are representative of the metabolic pathways of said animals;

analyzing the samples to detect the individual electrochemically active constituents representative of the metabolic pathways of said animals by passing the samples containing body fluid from said animals sequentially through (a) a liquid chromatograph column for achieving time-space separation of the constituents eluting from the column and (b) an electrochemical detection apparatus comprising a plurality of coulometric cells arranged in series;

maintaining the coulometric electrodes of said cells at different potentials, said cells operating at progressively varying potentials along the path of flow of eluant through the cells, said plurality of cells being sufficient in number to separate by measuring potentials of those relevant electrochemically active constituents coeluted from the chromatographic column at any instant of time, and recording the results of such coulometric measurements so as to separate said measurements by measuring potential as well as time of elution;

comparing the recording results thus obtained with like coulometric measurements of body fluids taken from other individual species of said animals and thereby identifying any differences between the various metabolic pathways of said representative electrochemically active constituents as well as unknown metabolites; and identifying those compounds which effect the presence and concentration of the representative electrochemically active constituents of the metabolic pathways; and administering to said animals those of said compounds which provoke a change in said metabolic pathways and representative electrochemically active constituents substantially to approach that found in body fluid or other animals.

* * * * *

UNITED STATES PATENT AND TRADEMARK OFFICE
CERTIFICATE OF CORRECTION

PATENT NO. : 5,104,639

DATED : April 14, 1992

INVENTOR(S) : Wayne R. Matson

It is certified that error appears in the above-identified patent and that said Letters Patent is hereby corrected as shown below:

"Claim 10, col. 23, line 6, after "fluids", insert --samples--."

"Claim 18, col. 23, line 67, after "fluids", insert --samples--."

"Claim 22, col. 24, line 51, after "fluids", insert --samples--."

"Claim 23, col. 26, line 34, "or" should be --of--."

Signed and Sealed this

Twenty-second Day of February, 1994

Attest:

BRUCE LEHMAN

*Attesting Officer*  *Commissioner of Patents and Trademarks*